(12) United States Patent
Mrochen et al.

(10) Patent No.: US 7,544,194 B2
(45) Date of Patent: Jun. 9, 2009

(54) METHOD OF GENERATING A CONTROL PROGRAM FOR A DEVICE FOR PHOTOREFRACTIVE CORNEAL SURGERY OF THE EYE

(75) Inventors: Michael Mrochen, Dresden (DE); Maik Kaemmerer, Dresden (DE); Theo Seiler, Zell (DE)

(73) Assignee: Wavelight Technologie AG, Erlangen (DE)

( * ) Notice: Subject to any disclaimer, the term of this patent is extended or adjusted under 35 U.S.C. 154(b) by 326 days.

(21) Appl. No.: 11/109,180

(22) Filed: Apr. 19, 2005

(65) Prior Publication Data
US 2005/0187540 A1    Aug. 25, 2005

Related U.S. Application Data

(62) Division of application No. 10/031,107, filed as application No. PCT/EP01/04978 on May 3, 2001, now Pat. No. 6,887,231.

(30) Foreign Application Priority Data
May 11, 2000  (DE) ................... 100 22 995

(51) Int. Cl.
A61B 18/18    (2006.01)
(52) U.S. Cl. .................. 606/5; 606/4; 128/898
(58) Field of Classification Search ............ 606/4–6; 128/898
See application file for complete search history.

(56) References Cited

U.S. PATENT DOCUMENTS

| | | | |
|---|---|---|---|
| 5,098,426 A * | 3/1992 | Sklar et al. ............. 606/5 |
| 5,163,934 A | 11/1992 | Munnerlyn | |
| 5,425,727 A | 6/1995 | Koziol | |
| 5,683,379 A | 11/1997 | Hohla | |
| 5,740,815 A | 4/1998 | Alpins | |
| 5,827,264 A * | 10/1998 | Hohla ............. 606/5 |
| 5,843,070 A | 12/1998 | Cambier et al. | |
| 6,099,522 A * | 8/2000 | Knopp et al. ............. 606/10 |
| 6,245,059 B1 | 6/2001 | Clapham | |

(Continued)

FOREIGN PATENT DOCUMENTS

DE    19702335    8/1998

(Continued)

OTHER PUBLICATIONS

Theo Seiler and Josef Wollensak; "Fundamental Mode Photoalblation of the Cornea for Myopic Correction," Lasers and Light in Opthalmology, vol. 5, No. 4, pp. 199-203 (1993).

(Continued)

*Primary Examiner*—Ahmed M Farah
(74) *Attorney, Agent, or Firm*—Haynes and Boone, LLP

(57) ABSTRACT

In a method of generating a control program, according to which a laser-beam spot is guided, while being controlled with respect to position and time, over a cornea to be corrected photorefractively, so as to ablate a predetermined ablation profile therefrom, the effect of the angle between the laser beam and the corneal surface on the energy density of the laser-beam spot incident on the corneal surface and/or on the fraction of the laser-beam energy incident on the corneal surface which is reflected away, is taken into account when generating the control program.

15 Claims, 8 Drawing Sheets

U.S. PATENT DOCUMENTS

| | | |
|---|---|---|
| 6,413,251 B1 | 7/2002 | Williams |
| 6,530,917 B1 * | 3/2003 | Seiler et al. ............... 606/5 |
| 6,572,606 B2 * | 6/2003 | Kliewer et al. ............. 606/5 |
| 6,673,062 B2 * | 1/2004 | Yee et al. ................... 606/5 |
| 6,887,231 B2 * | 5/2005 | Mrochen et al. ............ 606/5 |

FOREIGN PATENT DOCUMENTS

| | | |
|---|---|---|
| EP | 1060710 | 12/2000 |
| WO | WO 00/45759 | 8/2000 |
| WO | WO 01/50945 | 7/2001 |

OTHER PUBLICATIONS

John Shimmick, et al. "Corneal Ablation Profilometry and Steep Central Islands," Journal of Refractive Surgery, vol. 13, pp. 235-245 (May/Jun. 1997).

Junzhing Liang, et al. "Objective Measurement of Wave Aberrations of the Human Eye with the Use of a Hartmann-Shack-Wave Front Sensor" Optical Society of America, vol. 11, No. 7, pp. 1949-1957 (Jul. 1994).

Howland, et al. "A Subjective Method for the Measurement of Monochromatic Aberrations of the Eye" Optical Society of America, vol. 67, No. 11, pp. 1508-1518 (Nov. 1977).

Mierdel, et al. "Messplatz zur Bestimmung der momochromatischen Aberration des menschlichen Auges" Der Opthalmologe, pp. 441-445 (1997) not translated.

GH Pettit, et al. "Corneal-Tissue Absorption Coefficients for 193- and 213-nm Ultraviolet Radiation" Applied Optics, vol. 35, p. 3386-3391 (1996).

* cited by examiner

METHOD OF GENERATING A CONTROL PROGRAM FOR A DEVICE FOR PHOTOREFRACTIVE CORNEAL SURGERY OF THE EYE

CROSS-REFERENCE

This application is a divisional of U.S. application Ser. No. 10/031,107, filed Jan. 10, 2002 now U.S. Pat. No. 6,887,231; which is a 371 application of PCT/EP01/04978 filed May 3, 2001; which claims priority to German application 100 22 995.6, filed May 11, 2000.

BACKGROUND

The invention relates to a method of generating a control program, according to which a laser-beam spot is guided, while being controlled with respect to position and time, over a cornea to be corrected, so as to ablate a predetermined ablation profile therefrom. The invention also relates to an electronic computer and to a device for corneal surgery of the eye, in which a control program generated by means of the method is used.

Photorefractive keratectomy has become a widely established method of correcting lower-order visual disorder, for example myopia, hyperopia, astigmatism, myopic astigmatism and hyperopic astigmatism. The term "photorefractive keratectomy (PRK)" is usually understood as meaning only intervention on the corneal surface, after the so-called corneal epithelium has been removed. After the epithelium is removed, the Bowman's membrane, or corneal stroma, is exposed and can be ablated using a laser. Distinction is generally made between PRK and the LASIK method (Laser In Situ Keratomileusis). In the LASIK method, a so-called microkeratome is firstly used to excise an approximately 100 μm to 200 μm-thick corneal flap with a diameter of from 8 to 10 mm, leaving only a small remnant which acts as a "hinge". This flap is folded to the side, and then material is ablated (removed) by means of laser radiation directly in the stroma, i.e. not at the corneal surface. After the laser treatment, the cover is folded back to its original place, and relatively fast healing generally takes place.

The invention described below is suitable both for the aforementioned PRK and, in particular, for the LASIK technique.

In PRK and in LASIK, material of the cornea is ablated. The ablation is a function of the laser beam's energy density (energy per unit area) incident on the cornea. Various techniques for shaping the beam and guiding the beam are known, for example so-called slit scanning, in which the radiation is guided, by means of a moving-slit, over the area to be processed, so-called spot scanning, in which a radiation spot of very small dimensions is guided over the region to be ablated, and so-called full ablation, or wide-field ablation, in which the radiation is projected with a wide field over the full area to be ablated, and where the energy density changes across the beam profile in order to achieve the desired ablation of the cornea. For the said forms of beam guidance, the prior art contains respectively suitable algorithms for controlling the radiation, in order to ablate the cornea in such a way that the desired radius of curvature is finally imparted to the cornea.

The "spot scanning" already mentioned above uses a laser beam which is focused onto a relatively small diameter (0.1-2 mm), which is directed at various positions on the cornea by means of a beam-guiding instrument and which is successively moved, by a so-called scanner, so that the desired ablation from the cornea is finally achieved. The ablation hence takes place according to a so-called ablation profile. In particular, so-called galvanometric scanners can be used in PRK and LASIK (cf. the article by G. F. Marshall in LASER FOCUS WORLD, June 1994, p. 57). Since then, other scan techniques have been disclosed for guiding the laser beam.

According to the prior art, the said lower-order visual disorders (e.g. myopia, hyperopia, astigmatism) are currently performed [sic] according to the so-called refraction data of the patient's eye, i.e. the dioptric value measured for the patient's eye dictates the ablation profile according to which material will be removed (ablated) from the cornea (cf. T. Seiler and J. Wollensak in LASERS AND LIGHT IN OPHTHALMOLOGY, Vol. 5, No 4, pp. 199-203, 1993). According to this prior art, for a given patient's eye with a particular dioptric value, the laser radiation is hence guided over the cornea in such a way that a predetermined ablation profile is removed, for example according to a parabola when correcting myopia. In other words: the ablation profile is matched to the individual eye only according to the dioptric value, but not according to local non-uniformities of the "eye" optical system.

The article by J. K. Shimmick, W. B. Telfair et al. in JOURNAL OF REFRACTIVE SURGERY, Vol. 13, May/June 1997, pp. 235-245, also describes the correction of lower-order sight defects by means of photorefractive keratectomy, where the photoablation profiles correspond to theoretical parabolic shapes. Furthermore, this citation only proposes that a few empirical correction factors, which take account of the interaction between the laser and the tissue, be added in to the ablation profile in order thereby to achieve paraboloidal ablation on the eye.

A particular problem in photorefractive keratectomy and LASIK involves the relative positioning of the laser beam and the eye. The prior art contains various methods for this, for example so-called eye-trackers, i.e. instruments which determine the eye's movements so that the laser beam used for the ablation can then be controlled (tracked) in accordance with the ocular movements. The prior art relating to this is described, for example, by DE 197 02 335 C1.

As mentioned above, the methods of photorefractive corneal surgery in the prior art for correcting lower-order visual disorder are essentially "wholesale" methods, in so far as the correction is based on the (wholesale) dioptric value of the eye. Such lower-order visual disorder can be corrected, for example, by spherical or astigmatic lenses, or indeed by photorefractive correction of the cornea.

However, the optical imaging in the eye is impaired not only by the said lower-order visual disorders, but also by so-called higher-order image defects. Such higher-order image defects occur, in particular, after operative interventions on the cornea and inside the eye (cataract operations). Such optical aberrations can be the reason why, despite medical correction of a lower-order defect, full visual acuity (sight) is not achieved. P. Mierdel, H.-E. Krink, W. Wigand, M. Kaemmerer and T. Seiler describe, in DER OPHTALMOLOGE [THE OPHTHALMOLOGIST], No 6, 1997, p. 441, a measuring arrangement for identifying the aberration of the human eye. With such a measuring arrangement, it is possible to measure aberrations (imaging defects) for monochromatic light, and moreover not only aberrations due to the cornea, but also the imaging defects caused by the entire ocular imaging system of the eye can be measured, and actually as a function of position, i.e. with a particular resolution it is possible to determine, for given locations inside the pupil of the eye, how great is the imaging defect of the entire optical system of the eye to be corrected, at this position. Such imaging defects of the eye are mathematically described as a so-called wavefront aberration in the work by P. Mierdel et al. cited above. The term "wavefront aberration" is used to mean the spatial variation of the distance between the actual light wavefront from a central light point and a reference surface, e.g. its ideal spherical configuration. For instance, the sphere surface of the ideal wavefront is used as the spatial reference system. As the reference system for measuring the aberration, a plane is chosen when the ideal wavefront to be measured is plane.

The measuring principle according to the said work by P. Mierdel, T. Seiler et al. is also used in PCT/EP00/00827. It essentially involves splitting a parallel beam bundle of sufficient diameter through a hole mask into separate parallel individual beams. These individual beams pass through a converging lens (the so-called aberroscope lens) so that they are focused at a particular distance in front of the retina in the case of an emmetropic eye. The result is highly visible projections of the mask holes on the retina. This retinal light-point pattern is imaged, according to the principle of indirect ophthalmoscopy, onto the sensor surface of a CCD video camera. In the aberration-free ideal eye, the imaged-light-point pattern is undistorted and corresponds exactly to the hole-mask pattern. If there is an aberration, however, then individual displacements of each pattern point occur, because each individual beam passes through a particular corneal or pupillary area and experiences a deviation from the ideal path according to the non-uniform optical effect. From the retinal pattern-point displacements, the wavefront aberration is finally determined by an approximation method as a function of position over the pupillary surface. The said prior art also describes the mathematical representation of this wavefront aberration in the form of a so-called "wavefront-aberration hill". Above each pupillary location (x-y coordinates), this "wavefront-aberration hill" indicates a value of the wavefront aberration $W(x,y)$ which is then plotted as a height above the x-y coordinates. The higher the "hill" is, the greater are the imaging consumptions [sic] in the eye at the respective pupillary location. For each incident light beam, there is to first approximation a proportionality between the measured deviation of the corresponding retinal light point from its ideal position and the gradient of the "wavefront-aberration hill". The wavefront aberration can hence be identified from this as a function of position, with respect to an arbitrary reference value on the optical axis of the system. Ideal, in general undistorted light-point positions on the retina, which can yield the reference value, are for example four central points at a small distance from one another. Such points represent a central corneal/pupillary zone of about 1 to 2 mm in diameter, which from experience can be assumed to be substantially free of higher-order image defects.

The "wavefront-aberration hill" can be mathematically represented in various ways with the use of a closed expression (a function). Suitable examples include approximations in the form of a sum of Taylor polynomials or, in particular, Zernike polynomials. The Zernike polynomials have the advantage that their coefficients have a direct relationship with the well known image defects (aperture defects, coma, astigmatism, distortion). The Zernike polynomials are a set of completely orthogonal functions. An article by J. Liang, B. Grimm, S. Goelz and J. F. Bille, "Objective Measurement of Wave Aberrations of the Human Eye with the use of a Hartmann-Shack Wavefront Sensor", *Optical Society of America*, 11(7): 1949-1957, July 1994, shows how the wavefront (or wavefront aberration) can be calculated from the grid-point displacements. From identifying the derivative function of the wavefront, it is hence possible to determine the actual wavefront. The wavefront is found as the solution of a system of equations. The article by H. C. Howland and B. Howland, "A Subjective Method for the Measurement of Monochromatic Aberrations of the Eye", *Journal of the Optical Society of America* 67(11): 1508-1518, November 1977, also describes a method for identifying monochromatic aberration and the determination of the first fifteen Taylor coefficients.

The device proposed in the aforementioned PCT/EP00/00827 for photorefractive corneal surgery in the case of higher-order sight defects has the following instruments:
  an aberroscope for measuring the wavefront aberration of the entire optical system of the eye to be corrected, with respect to a particular ocular position,
  means for deriving a photoablation profile from the measured wavefront aberration so that photoablation according to the photoablation profile minimises the wavefront aberration of the eye being treated, and
  a laser-radiation source and means for controlling the laser radiation with respect to the particular ocular position, in order to ablate the photoablation profile.

And, if this device produced significant improvements compared with the previous solutions, it was found that the treatment successes in some cases were not as good as might have been expected in view of the accuracy with which the photoablation profile had been compiled.

It is therefore an object of the present invention to provide a way in which even better treatment successes can be achieved.

The invention is based on the discovery that in the prior art, although a very accurate ablation profile was determined, the simplifying assumption was nevertheless made, when carrying out the ablation, that the laser beam induces uniform ablation at each location on the cornea. However, the laser beam is incident with different angles at the various locations on the cornea. This has two consequences: on the one hand, the density of the laser-beam energy incident on the corneal surface changes with this angle and, on the other hand, a differing fraction of the incident laser radiation is reflected depending on the angle.

The invention correspondingly provides a method of generating a control program of the generic type mentioned in the introduction, in which, when generating the control program, the effect of the angle between the laser beam and the corneal surface on the energy density of the laser-beam spot incident on the corneal surface is taken into account.

Alternatively or additionally, account is taken of the fact that a fraction of the laser-beam energy incident on the corneal surface is reflected away.

SUMMARY

Preferably, in this case, formulae that are described more explicitly below are employed.

The invention can even be used when not just one laser-beam spot is applied to the cornea, but rather a full laser-beam profile, as in the full ablation mentioned in the introduction and in slit scanning.

The invention furthermore relates to a program medium, as well as to an electronic computer for delivering control signals to control a laser beam, the computer being programmed with a control program generated according to the said method, which it runs when delivering the control signals.

The invention furthermore relates to a device for photorefractive corneal surgery of the eye to correct sight defects, having:
  an instrument for measuring the optical system of the eye to be corrected,
  means for deriving an ablation profile from the measured values, a laser-radiation source and means for controlling the laser radiation, the control means comprising an electronic computer which runs a control program that has been generated using the method according to the invention.

BRIEF DESCRIPTION OF THE DRAWINGS

An exemplary embodiment of the invention will be explained in more detail below with the aid of the drawings, in which.

DETAILED DESCRIPTION

Figure 1:
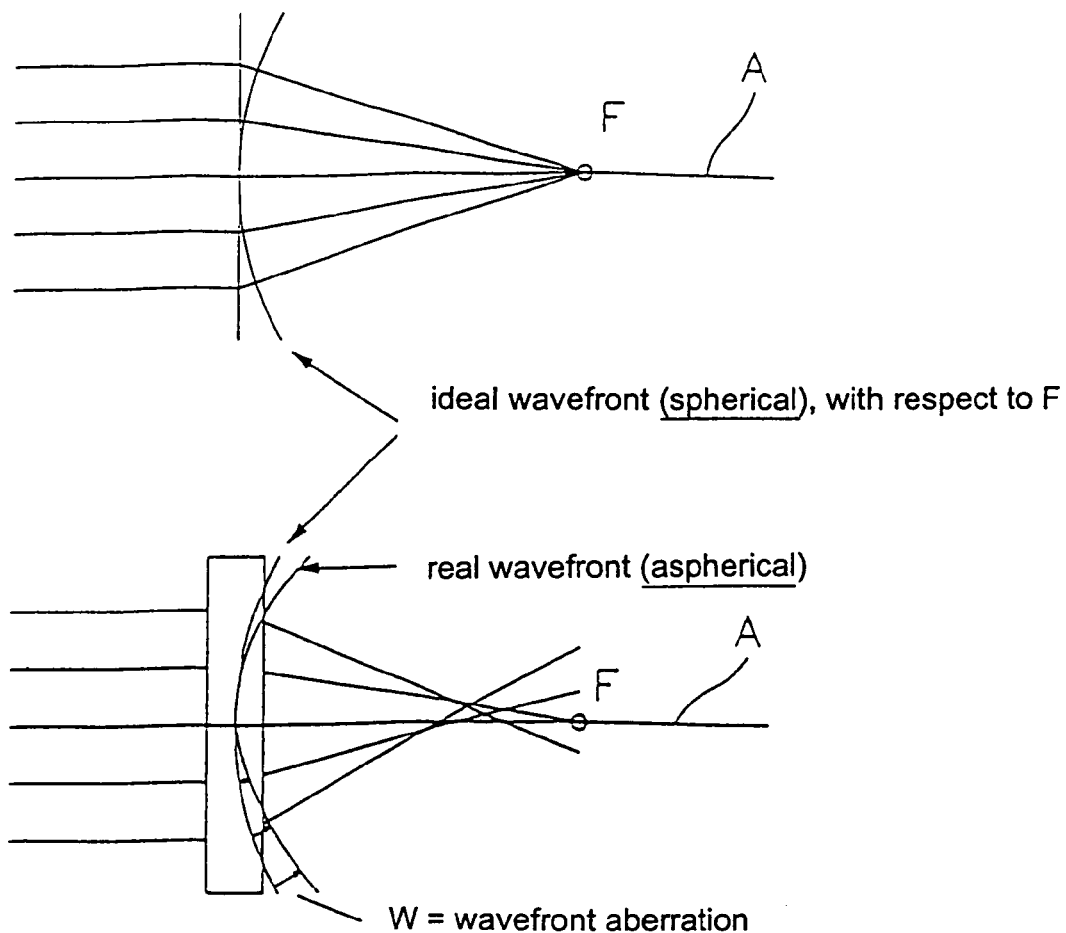
FIG. 1 schematically shows the wavefront aberration.

FIG. 1 schematically shows the aforementioned wavefront aberration of an eye, i.e. the deviation of the real, aspherical wavefront from the ideal wavefront. A is the optical axis of the system and F is the focal point, which is also the imaginary starting point of the radiation in the case of an ideal wavefront.

Figure 2:
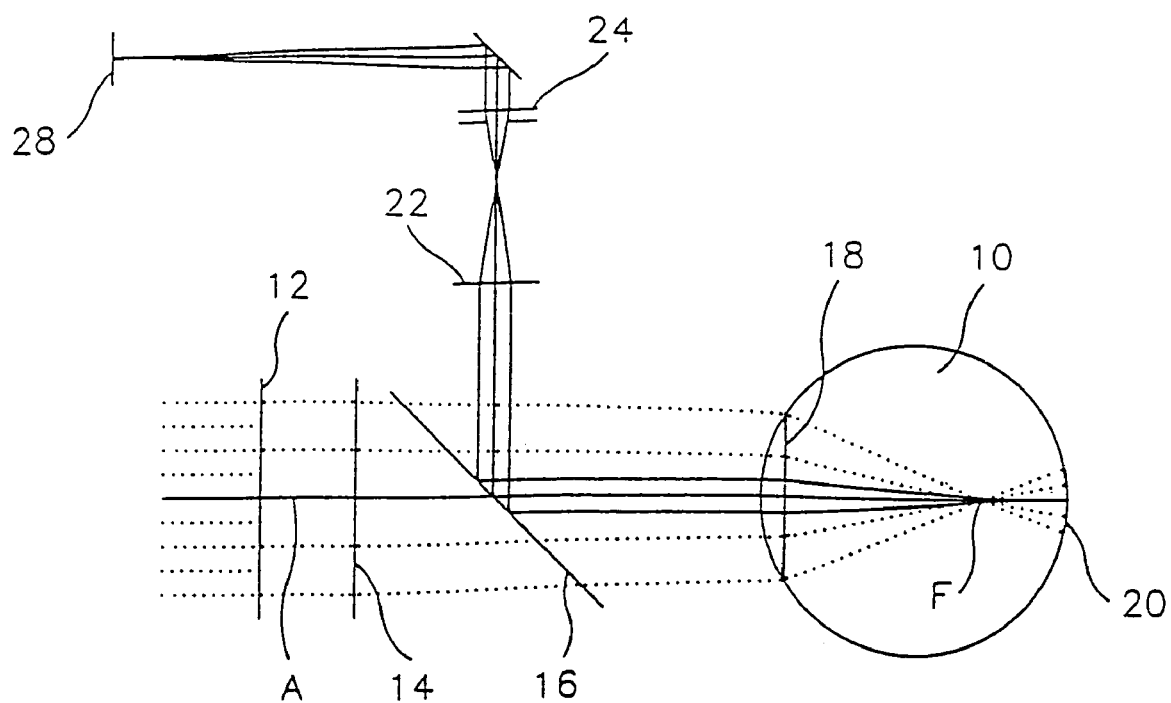
FIG. 2 schematically shows an aberroscope for measuring the wavefront aberration of the entire optical system of an eye to be treated.

FIG. 2 schematically shows the optical layout of a video aberroscope for measuring the wavefront aberration of an eye 10. The green light from a HeNe laser (543 nm) is broadened to a diameter of approximately 12 mm and subsequently split by means of a hole mask 12, in which a plurality of equidistant holes are formed, into a corresponding number of parallel individual beams. According to FIG. 2, these individual beams, which are indicated only schematically by dotted lines, run parallel to the optical axis A of the system. Using an aberroscope lens 14 (converging lens) in front of the eye 10, these beams are refracted in such a way that they are focused at a particular distance in front of the retina 20 (focus F). In the case of an eye with correct version, the aberroscope lens has e.g. a power of +4 dpt. In the aberration-free ideal eye, a completely undistorted light-point pattern is produced on the retina 20. The pupil is indicated by the reference number 18.

If the eye 10 has an aberration, however, then the pattern points will be displaced according to the imaging defects, since each individual beam passes only through a very particular location in the pupil 18 and experiences a deviation from the ideal path according to the non-uniform optical effects. This deviation from the ideal path corresponds to the optical imaging defect of the entire optical system of the eye 10 with the respect to a light beam which passes through the particular location inside the pupil. On the cornea, the individual beams have e.g. a constant separation of 1.0 mm in the x and y directions, and their diameter is for example approximately 0.5 mm. The entire parallel measurement-beam bundle has e.g. a size of 8×8 mm on the cornea.

By means of a semi-silvered mirror 16, the light-point pattern produced on the retina 20 is imaged via an ophthalmoscope lens 22 and an objective 24 for the retinal image onto a sensor surface 28 of a solid-state image camera (CCD camera) so that the resulting light-point pattern can be processed by a computer. The deviations of the locations of the light points, with respect to the equidistant, uniform structure of the defect-free eye, provides the opportunity to determine the wavefront aberration W(x,y) as a function of position over the pupillary surface of the eye. The function of position can be approximated by using a set of polynomials, e.g. Taylor polynomials or Zernike polynomials. The Zernike polynomials are preferred here because their coefficients $C_i$ have the advantage of a direct relationship with the image defects, such as aperture defects, coma, astigmatism, distortion. With the Zernike polynomials $Z_i(x,y)$, the wavefront aberration W can be represented as follows:

$$W(x,y) = \Sigma_i C_i \times Z_i(x,y).$$

The Cartesian coordinates in the pupillary plane are denoted (x,y).

By identifying e.g. the first 14 coefficients $C_i$ (i=1, 2, ..., 14) of the Zernike polynomials, it is possible to obtain a sufficiently accurate description of the wavefront aberration W(x,y) as a function of the position coordinates of the free pupillary surface. This provides a so-called wavefront-aberration hill, i.e. in a three-dimensional representation, a function above the position coordinates x,y which indicates the local imaging defects in each case. Apart from the Zernike polynomials, it is also possible to choose other options for mathematically describing the wavefront, e.g. Taylor series. The Zernike polynomials are merely the exemplary embodiment selected here.

Figure 3:
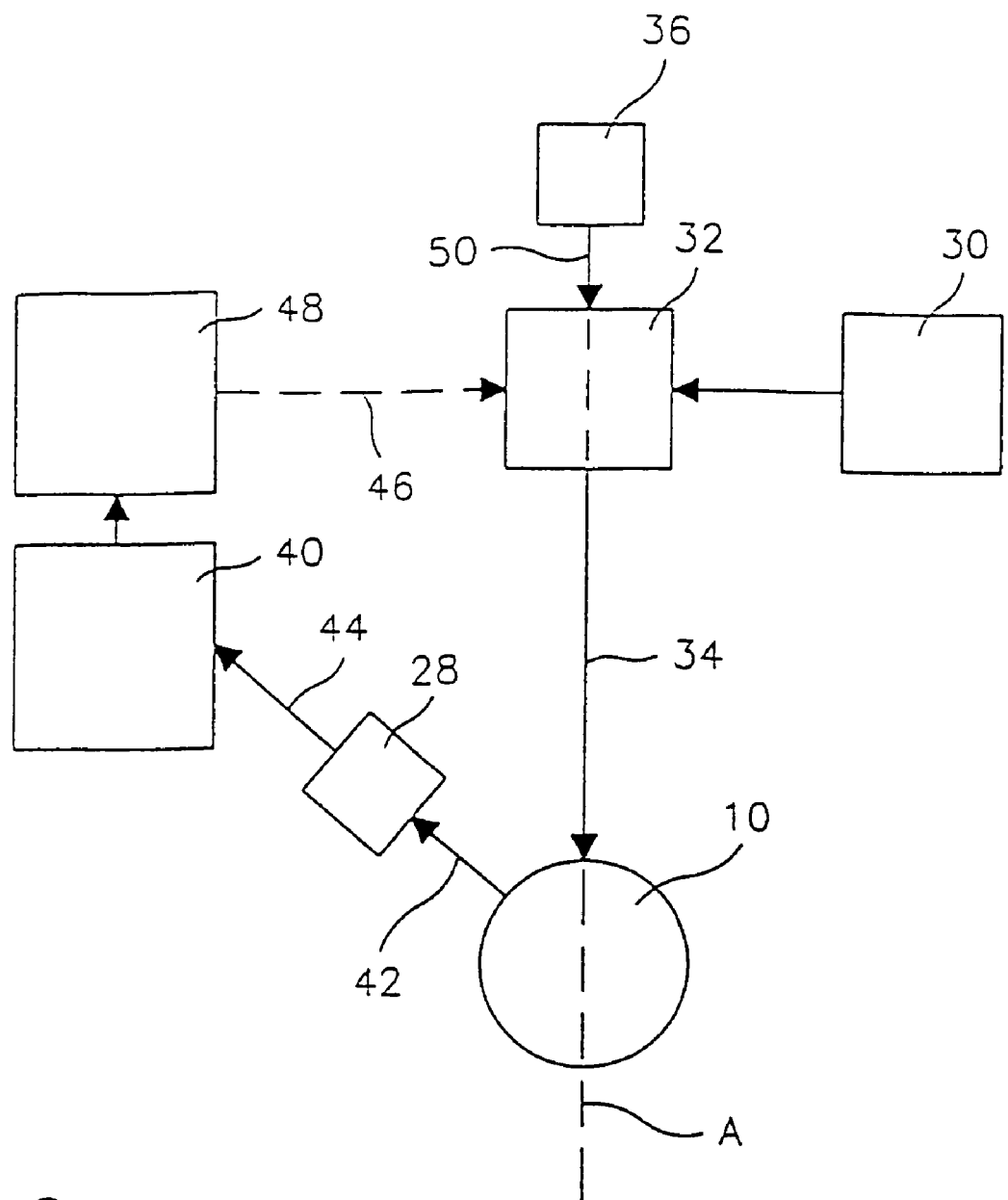
FIG. 3 schematically shows a measuring and control arrangement for carrying out photorefractive keratectomy of the eye, with means for deriving a photoablation profile and means for controlling the laser beam.

From this wavefront aberration W(x,y), a so-called photbablation profile is calculated by using a computer 48 (FIG. 3). The computer hence finally determines, from the light-point pattern, the wavefront aberration in the form of a particular number of Zernike coefficients and then determines, from the wavefront aberration, a photoablation profile, i.e. data concerning the depth to which the cornea needs to be removed (ablated) at the respective pupillary location in order to reduce the wavefront aberration. The ablation profile, i.e. the layer thickness of the material to be removed as a function of position (X-Y coordinates) can be identified from the wavefront (aberration) in various ways:

Basically, the ablation profile for an eye to be corrected is calculated using a corresponding eye model.

To that end, the wavefront aberration is mathematically projected onto the corneal surface while taking into account the geometrical properties of the eye, e.g. the thickness of the cornea, the distance between the back surface of the cornea and the front surface of the lens, the distance between the front surface of the lens and the back surface of the lens, and the distance between the back surface of the lens and the retina. The refractive indices of the individual optical elements of the eye are furthermore taken into account when calculating the ablation profile. The wavefront essentially describes the differences in the time of flight of the light, i.e. the optical path distance. If the optical path difference is divided by the refractive index, then the geometrical path is obtained. From the projection of the wavefront onto the cornea, it is hence possible to derive the associated ablation profile. In the form of an iteration, an ablation depth (in LASIK, correspondingly a depth of the material ablated in the stroma) is mathematically assumed at the given location on the cornea, and the effect which such ablation would cause on the time-of-flight differences of the beams is calculated. The aim is to equalise the times of flight of the beams at all locations on the cornea, so that the wavefront aberration will become as small as possible. In this, case, it is necessary to take into account that the wavefront can also assume values whose physical meaning implies addition of tissue (i.e. thickening of the cornea), which is not generally possible. The ablation profile must therefore be adapted accordingly, i.e. shifted overall so that the desired target profile of the cornea will be achieved only by ablation (removal) of tissue.

The wavefront aberration can be calculated not only in the pupillary plane (entrance pupil), but also directly at the cornea. When the corresponding refractive indices are taken into account, the actual ablation profile for a particular pupillary diameter is hence obtained.

A correction for the wavefront aberration $W(x,y)$ used to determine the ablation profile is made so as to take the eye's healing process after the operation into account as well. This is because the healing process leads to a change in the optical properties of the eye, and [lacuna] that these changes [sic] ought to be taken into account in the basic wavefront aberration in order to achieve the best results. This is done as follows:

So-called correction factors ("fudge factors") $A_i$ are introduced into the equation above, in which the wavefront aberration $W(x,y)$ is represented as a sum of Zernike polynomials $Z_i(x,y)$:

$$W(x, y) = \sum_{i=0}^{n} A_i \times C_i \times Z_i(x, y)$$

In comparison with the formula above, correction factors $A_i$, which empirically take account of the wound-healing process, have respectively been added in the sum of Zernike, coefficients and Zernike polynomials. In other words: the above function $W(x,y)$ describes the wavefront to be corrected at the eye while taking into account postoperative changes of individual optical image defects ($Z_i$) due to the wound healing. In this case, the Zernike coefficients of zeroth to eighth order, in particular, are clinically relevant. As already explained above, the polynomial coefficients $C_i$ describe the degree of the image defect from the described measurement.

It has been empirically shown that the clinically relevant value-range [sic] of the correction factors $A_i$ lies in the range of from −1000 to 0 to +1000. It has also been empirically determined that the clinical correction factors $A_i$ assume different values for each coefficient $C_i$. $A_i$ is hence a function of $C_i$. This functional dependency $A_i = f_i(C_i)$ differs for the individual coefficients $C_i$, i.e. the function $f_i$ has different forms for the individual coefficients $C_i$.

It has also been shown that the function $A_i = f_i(C_i)$ is furthermore dependent on the therapeutic laser system respectively used, since the postoperative healing process is itself also dependent on the laser system respectively used. This means that generally applicable (abstract) data or algorithms cannot in general be provided for the clinical correction factors $A_i$, and these correction factors must instead be empirically (experimentally) determined clinically for the laser system respectively used, the aforementioned typical value range of −1000 through 0 to +1000 being applicable, in particular, for the laser system from WaveLight, Erlangen, Germany which was used here.

As stated, when the aforementioned correction factors $A_i$ are not used, ablation profiles determined on the basis of the wavefront aberration can lead to overrating or underrating of individual image defects owing to the healing of the wound after the refractive intervention, for instance, in LASIK, the healing of the flap which had been folded back. To correct a coma of $Z_7 = 0.3$ μm, for instance, it is necessary to ablate a coma of about $Z_7 = 0.5$ μm from the cornea so that a $Z_7 = 0$ (here, "Z" stands for the Zernike coefficient as an example) is obtained at the end of the wound healing (e.g. epithelial closure, approximately 7 days).

The correction factors $A_i$ determined as indicated above will stored in the computer, and the computer program worked [sic] them (automatically) into the ablation profile that will finally be used.

As an alternative to the aforementioned calculation of the ablation profile from the wavefront aberration, the ablation profile may also be calculated directly from projection of points onto the cornea and the retina. If a light beam is incident with known angles of incidence and coordinate points on the cornea and then in the eye, then this light beam will be imaged onto the retina according to the optical properties of the eye. Since the position of the light beam on the cornea and the angle of incidence of the beam are known, the optical beam path can be reproduced by measuring the position of the light beam on the cornea. In this context, if it is found that the position of the light beam on the retina deviates from the target position (the target position means aberration-free imaging), then the aberration can be determined from the positional deviation. The light is refracted according to the geometrical curvature of the surface of the cornea and the further aberration defects of the "eye" system. The aforementioned positional deviation of the light beam on the retina can be expressed by a corresponding change in the angle of incidence of the light. The angle of incidence of the light is proportional to the derivative function of the surface of the cornea. Through an iterative procedure, a (pathological) change in the curvature of the corneal surface can be inferred from the positional shift of the light beam on the retina and the associated change in the angle of incidence of the light. The change in the curvature of the corneal surface hence describes the derivative function of the (desired) ablation profile. If this method is carried out with a sufficient number of light beams at different points in the eye (e.g. by projecting a grid onto the cornea), then the entire derivative function of the (desired) ablation profile can be identified. The ablation profile can be calculated from this by known mathematical methods (e.g. spline interpolation and subsequent integration).

It has been shown that in some cases, ablation profiles obtained by wavefront measurements make it necessary to have a so-called transition zone because, in the absence of such a transition zone, a certain residue of material could possibly be left at the edge of the ablation profile,. i.e. a step would be created on the cornea. In order to avoid such a step, an approximately 0.5 mm to 3 mm-wide transition zone is provided around the outside of the ablation profile, in order to guarantee a smooth, step-free surface on the entire cornea.

FIG. 3 schematically shows the computer system and control system for carrying out photoablation according to the computed photoablation profile. The photoablation takes place both superficially on the cornea and intra-stromally.

An example of a particularly suitable laser 30 for the photoablation is an excimer laser (193 nm). Also particularly suitable are Er:YAG solid-state lasers with a wavelength of 2.94 μm and UV solid-state lasers (e.g. Nd:YAG with 213 nm).

The laser radiation is deflected by means of a galvanometric scanner 32, and the deflected laser beam 34 is directed at the eye 10.

Coaxially with the laser beam 34, another beam from a so-called positioning light source 36 is directed at the eye 10. The beam 50 from the positioning light source 36 defines a reference axis A, whose position is fixed in space.

In the real case, the eye 10 moves with respect to the axis A. In order, in the event of such movements, to match (track) the processing beam 34, and hence the ablation profile to be removed, to the movements of the eye, the eye is illuminated with infrared radiation (not shown), and the CCD camera 28 is used to record images at a particular image repetition frequency. The image radiation 42 from the eye hence generates images in the CCD camera 28, which are electronically processed. The electronic output signal 44 from the camera 28 is sent to an image-processing instrument 40, and the result of the image processing is input into a computer 48, which both performs the evaluation and controls the scanner 32. The computer 48 hence outputs a corresponding control signal 46 to the scanner 32, so that the laser beam 34 is controlled in such a way that the ablation profile too is removed with respect to a particular ocular position, with respect to which the wavefront ablation [sic] was also measured. In this way, the optical defects of the entire eye can be corrected by photoablation of the cornea. The ablation profile removed here in the above sense is the ablation profile that was obtained from the wavefront measurement and was modified by the aforementioned empirical correction factors because of the wound healing.

The device described so far can also be found in PCT/EP00/00827. In order that the photoablation profile so elaborately computed can actually be implemented, the computer 48 is now programmed according to the present invention such that the effect of the angle between the laser beam and the corneal surface on the ablation depth is taken into account.

As already mentioned, there are two significant factors involved in this:

1) the laser-beam spot changes its size and shape as a function of angle when it is incident on a curved surface, so that the energy density of the incident laser beam changes, and 2) depending on the angle between the laser beam and the corneal surface, a different fraction of the incident laser energy is reflected away.

The effective, i.e. ablating energy density is hence reduced as a function of the angle between the laser beam and the corneal surface.

Dependency of the Ablation Depth on the Effective Energy Density

It is therefore necessary first of all to examine the way in which the different effective energy density affects the ablation depth.

Figure 4:
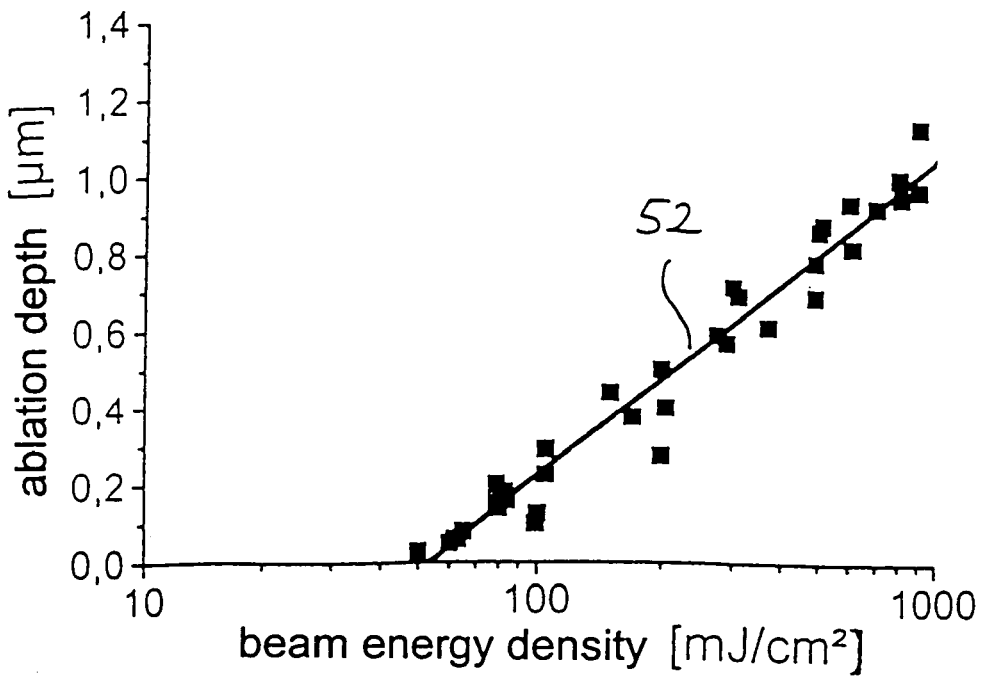
FIG. 4 shows the dependency of the ablation depth on the beam energy density.

This is represented in FIG. 4. The square points in this case stand for values measured with laser pulses of a particular length (for laser radiation from an ArF excimer laser with a wavelength of 193 nm). It can be seen that the ablation depth increases with the logarithm of the effective beam energy density. The ablation depth d therefore obeys the formula $$d = m \cdot \ln\left(\frac{F}{F_{th}}\right), \quad (1)$$

where F is the effective beam energy density and $F_{th}$ is an energy-density threshold above which ablation actually starts to take place. The factor m is a constant. The curve 52 was fitted according to this formula. The energy-density threshold $F_{th}$ was found to be 50 mJ/cm² in this case.

The fact that the ablation depth as a function of the effective beam energy density obeys such a simple formula facilitates numerical processing in the computer 48.

Incident Energy Density when Incident on the Curved Surface

The way in which the incident energy density changes as a function of the location of the incidence of the laser-beam spot on the cornea will now be examined below.

Figure 5:
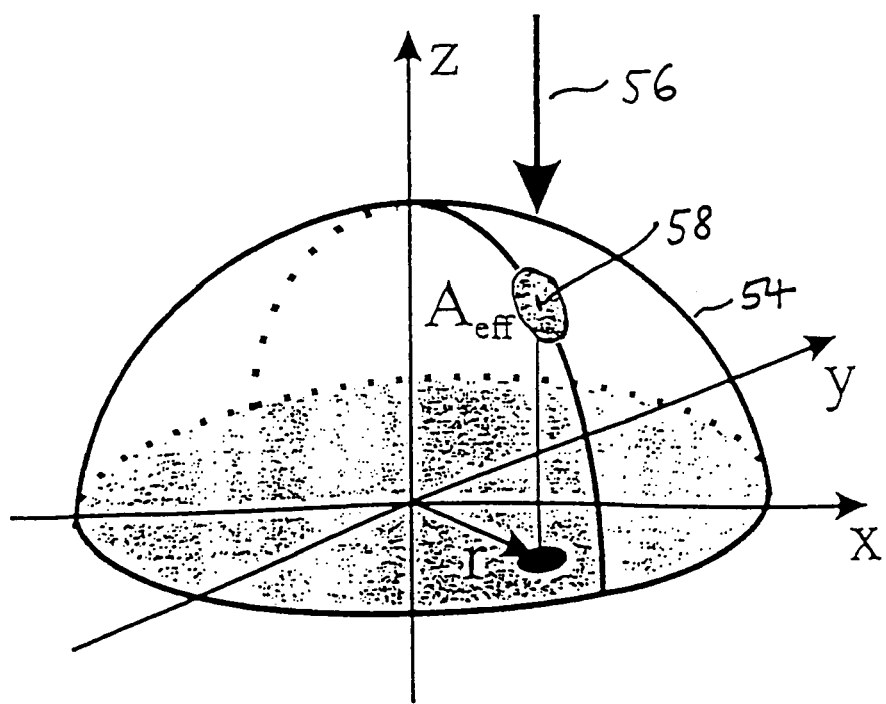
FIG. 5 schematically shows the surface of the cornea with a laser-beam spot incident on the surface and with axes shown.

FIG. 5 schematically shows the cornea 54, assumed to be spherical, on which a laser beam 56 is incident. Here, for simplicity, it is initially assumed that the laser beam 56 propagates parallel to the z axis. The laser-beam spot has an area $A_{eff}$ on the surface of the cornea 54.

The area $A_{eff}$ can now be calculated as a function of the coordinates of the incidence point of the laser-beam spot centre on the cornea 54.

In this case, only two of the coordinates are independent of each other, the third coordinate being given by the shape of the surface of the cornea 54. The following hence applies for the z coordinate as a function of the coordinates x and y:

$$z = f(x,y) = f(r) = \sqrt{R^2 - x^2 - y^2} = \sqrt{R^2 - r^2}. \quad (2)$$

Here, R is the radius of the corneal hemisphere. $r = \sqrt{X^2 + Y^2}$ is the distance from the z axis to the incidence point 58 of the laser-beam spot centre.

If $r_3$ is the radius of the laser-beam spot before incidence on the cornea, then the following is obtained for $A_{eff}(r)$:

$$A_{eff}(r) = \int_{-rz}^{rz} \int_{-\sqrt{r^2-z^2}+r}^{\sqrt{r^2-z^2}+r} \sqrt{1 + \left(\frac{d}{dx}f(x,y)\right)^2 + \left(\frac{d}{dy}f(x,y)\right)^2}\, dx\, dy. \quad (3)$$

(This formula is found in Chapter F of: Höhere Mathematik griffbereit [higher mathematics ready-reference], Akademie-Verlag, Berlin, 1972, pages 638 to 643.)

The area $A_{eff}$ of the cornea 54 is therefore greater by a factor k1(r), $$k1(r) = \frac{A_{eff}(r)}{A_0} = \frac{A_{eff}(r)}{\pi \cdot r_z^2}, \quad (4)$$

than the area $A_0$ of a laser-beam spot with normal incidence.

The beam energy density, moreover, is in fact defined as the ratio of the pulse energy of the laser E to the exposed A area, F=E/A. The density of the energy incident on the corneal surface is therefore reduced to the value F/k1(r) in relation to the energy density F of the incident laser-beam spot.

Thus, with the known logarithmic dependency of the ablation depth on the effective beam energy density, it is possible to set up a correction factor kor1(r), by which the ablation depth achieved with normal incidence of the laser-beam spot needs to be multiplied in order to obtain the ablation depth that is achieved in the case as represented in FIG. 5. This first correction factor is given as $$kor1(r) = \frac{\ln\left(\frac{F}{k1(r)F_{th}}\right)}{\ln\left(\frac{F}{F_{th}}\right)}. \quad (5)$$

Figure 6:
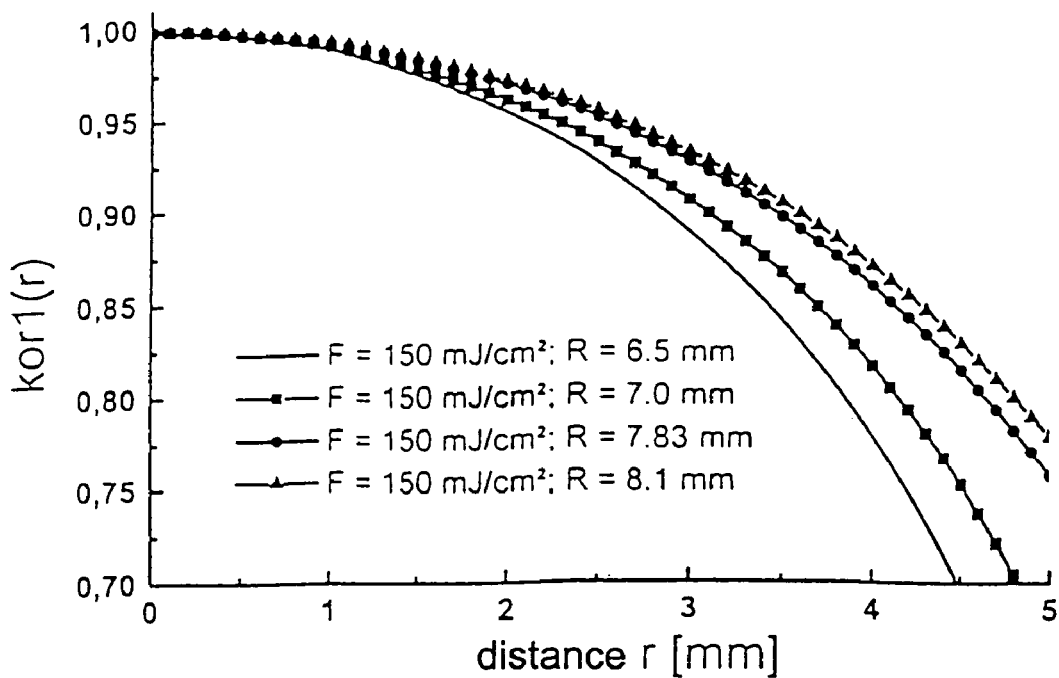
FIG. 6 shows the dependency of a first correction factor on the distance r of the incidence point of the laser-beam spot centre on the cornea from the z axis for different radii R of the cornea.

FIG. 6 shows numerically determined curves in this context for different radii R of the cornea 54.

As can be seen from FIG. 6, a significant deviation of the ablation depth from the value 1, which was assumed in the prior-art methods, is found towards the edge of the cornea.

The computer 48 is programmed in such a way that it compensates for this reduced ablation depth, that is to say, for example, a correspondingly greater number of laser-beam pulses are sent onto the relevant locations so that the desired photoablation profile will be achieved.

Effect of Surface Reflection

Figure 7:
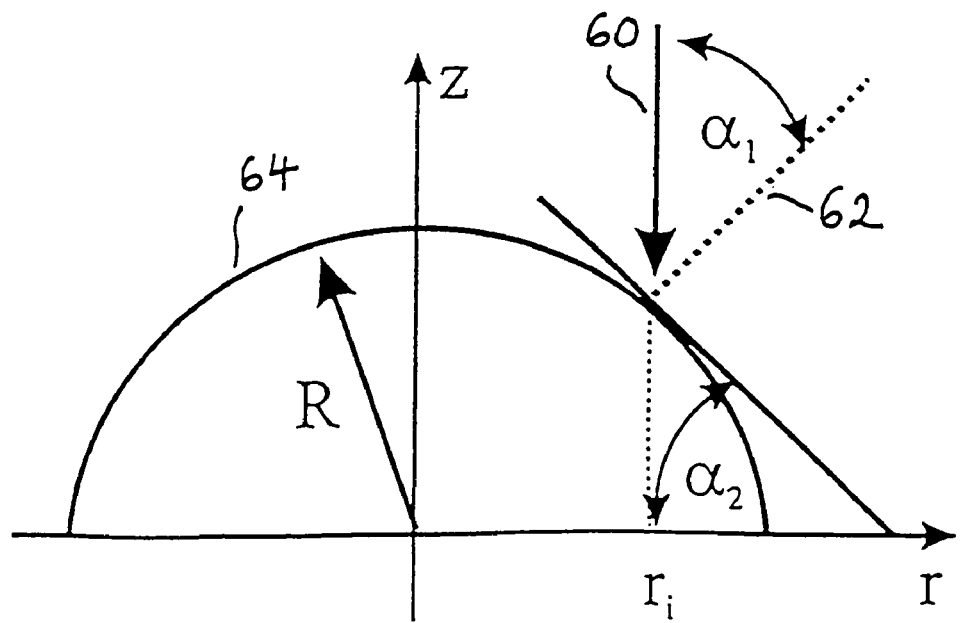
FIG. 7 schematically shows the surface of the cornea and the laser beam incident at the angle $\alpha_1$.

We will next consider the dependency of the ablation depth on the surface reflection. In FIG. 7, the incidence angle $\alpha_l$ between the incident laser beam 60 and the normal 62 to the surface of the cornea is defined, the cornea being represented here schematically in section as a semicircle 64.

To identify the reflected fraction of the incident light, use is made of the Fresnel equations, which can be found for example in the Lehrbuch der Experimentalphysik [textbook of experimental physics] by Bergmann, Schaefer, Volume III Optics, Walter de Gruyter, Berlin, N.Y. 1987, page 496:

$$q_\perp(\alpha_l) = \frac{\sqrt{n^2 - \sin^2(\alpha_l)} - \cos(\alpha_l)}{1 - n^2} \quad (6)$$

$$q_\parallel(\alpha_l) = \frac{n^2 \cos(\alpha_l) - \sqrt{n^2 - \sin^2(\alpha_l)}}{n^2 \cos(\alpha_l) + \sqrt{n^2 - \sin^2(\alpha_l)}}, \quad (7)$$

where $q\perp$ stands for perpendicularly polarised light and $q\|$ stands for parallel-polarised light and n is the refractive index of the corneal material, which is for example n=1.52 for a wavelength of 193 nm (see G. H. Pettit, M. N. Ediger, Corneal-tissue absorption coefficients for 193- and 213-nm ultraviolet radiation, Appl. Optics 1996, volume 35, pages 3386 to 3391). In order to obtain a dependency on the distance r, the following formula is used $$\alpha_l(r) = a\tan\left(\frac{r}{\sqrt{R^2 - r^2}}\right), \quad \text{where:} \quad 0 \le r^2 < R \text{ [sic]}. \quad (8)$$

For unpolarised light, the reflectance k2(r) at the interface between air and tissue is given as:

$$k2(r) = \frac{q_\perp^2(r) + q_\parallel^2(r)}{2}.$$

If only the fact that a part of the incident radiation is reflected away were to be taken into account, and the aforementioned reduction in the energy density due to the increase in the effective area $A_{eff}$ in relation to the original area $A_0$ were to be omitted, then an effective beam energy density of (1−k2(r))×F would be obtained in relation to the incident beam energy density F, and hence an attenuation of the ablation depth d to kor2(r)×d, where $$kor2(r) = \frac{\ln\left(\frac{(1-k2(r)) \cdot F}{F_{th}}\right)}{\ln\left(\frac{F}{F_{th}}\right)}. \quad (9)$$

Figure 8:
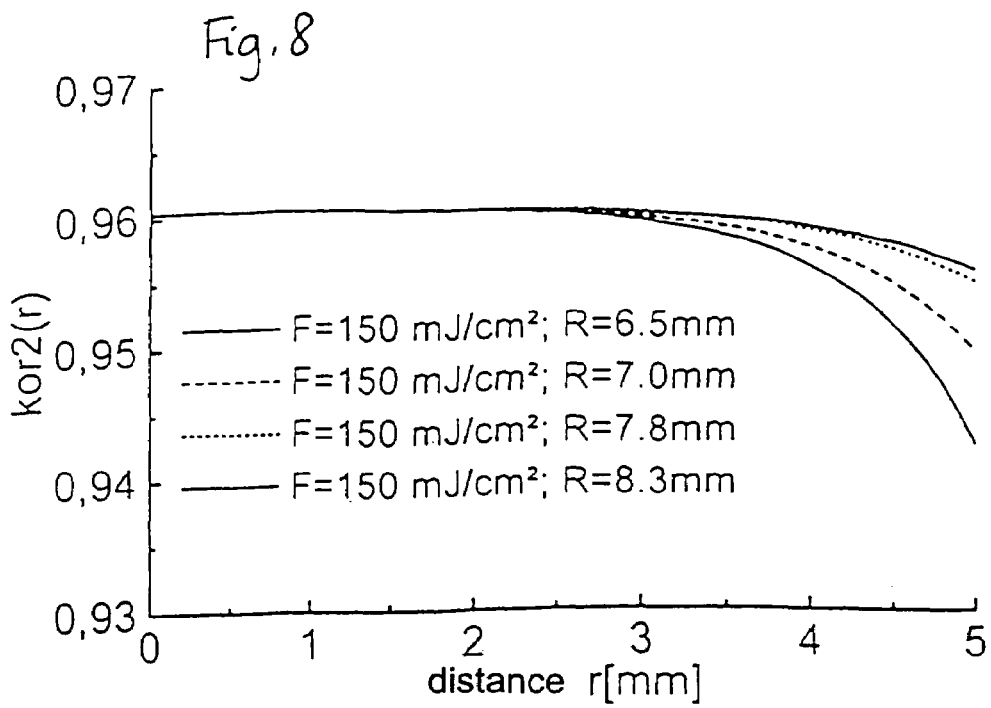
FIG. 8 shows the dependency of a second correction factor on the distance r of the incidence point of the laser-beam spot centre on the cornea from the z axis [lacuna] different radii R of the cornea.

FIG. 8 represents numerically determined curves which represented [sic] the variation of kor2 as a function of the distance r of the incidence point of the laser-beam spot centre on the cornea from the z axis for various radii R of the cornea 64. As can be seen, the drop in the ablation depth is very pronounced, especially at the edge, so that the defects apparently were particularly large in the prior art, where a value of 1 for kor2(r) was assumed even at the edge.

Combination of the Said Effects

Naturally, the two aforementioned phenomena, namely the increase in the effective area of the laser-beam spot and the reflection, ought to be taken into account in combination with each other:

Of the incident beam energy density F, a beam energy density F/k1(r) is incident on the corneal surface, and the fraction (1−k2(r))×F/k1(r) of this is not reflected away.

A combined correction factor kor(r) for the ablation depth is hence given as:

$$kor(r) = \frac{\ln\left(\frac{(1-k2(r)) \cdot F}{k1(r) \cdot F_{th}}\right)}{\ln\left(\frac{F}{F_{th}}\right)}. \quad (10)$$

Figure 9:
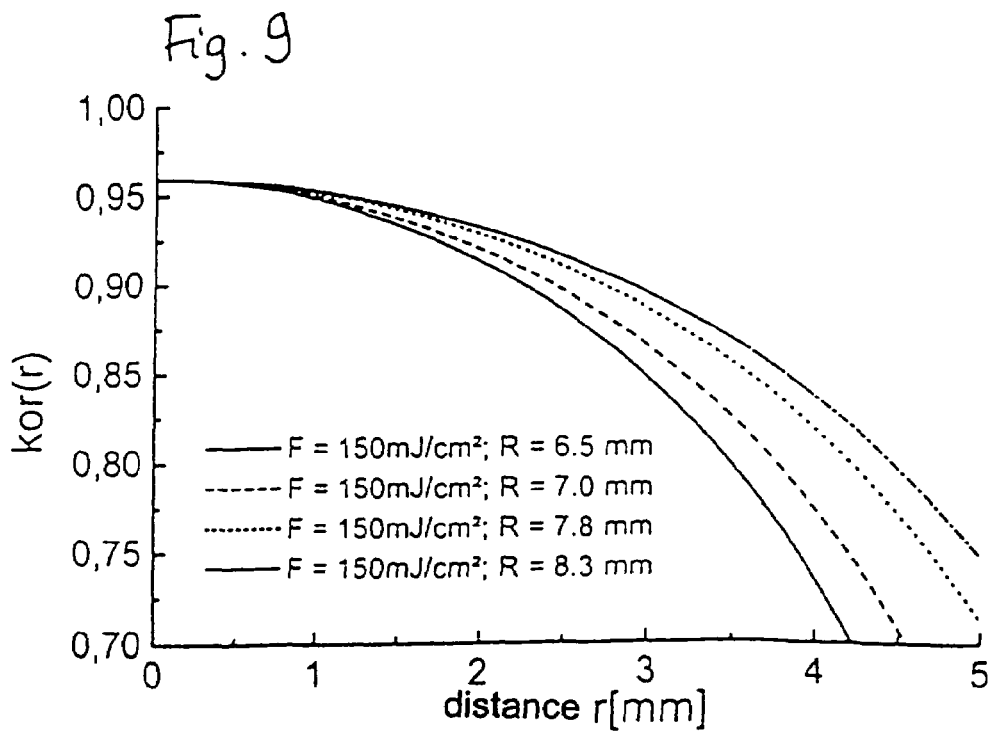
FIG. 9 shows the dependency of a combined correction factor for the ablation depth on the distance r of the incidence point of the laser-beam spot-centre on the cornea from the z axis for different radii R of the cornea.

The variation of this combined correction factor kor(r) is represented in FIG. 9 with the aid of numerically determined values as a function of the distance r of the incidence point of the laser-beam spot centre on the cornea from the z axis for different radii of curvature of the cornea with a beam energy density of 150 mJ/cm$^2$.

As can be seen in FIG. 9, the drop in the correction factor kor(r) towards the edge is commensurately steeper where the radius of curvature of the corneal surface is smaller.

Figure 10:
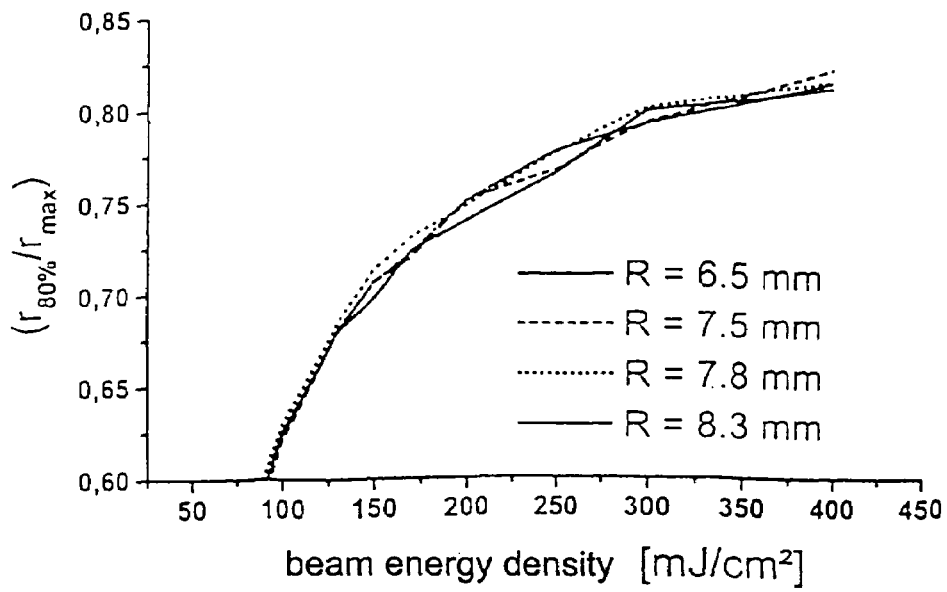
FIG. 10 shows the dependency of the ratio of the distance at which the density of the unreflected energy incident on the corneal surface is 80%, to the distance at which it is 0, on the beam energy density of the incident laser beam.

This can also be seen with the aid of FIG. 10. There, the distance $r_{80\%}$, at which $kor(r_{80\%})=0.8$, is divided by the value $r_{max}$, at which $kor(r_{max})=0$, and this ratio is plotted against the energy density of the incident laser beam.

With the approximation that the laser-beam spot is projected parallel to the z axis, it is already possible to obtain satisfactory results. If the laser beam is controlled by using the control program in the computer 48 so as to compensate for the reduction in the ablation depth at the edge of the cornea, more satisfactory healing results can be achieved for the patient's treatment.

Oblique Incidence of the Laser Beam

Figure 11:
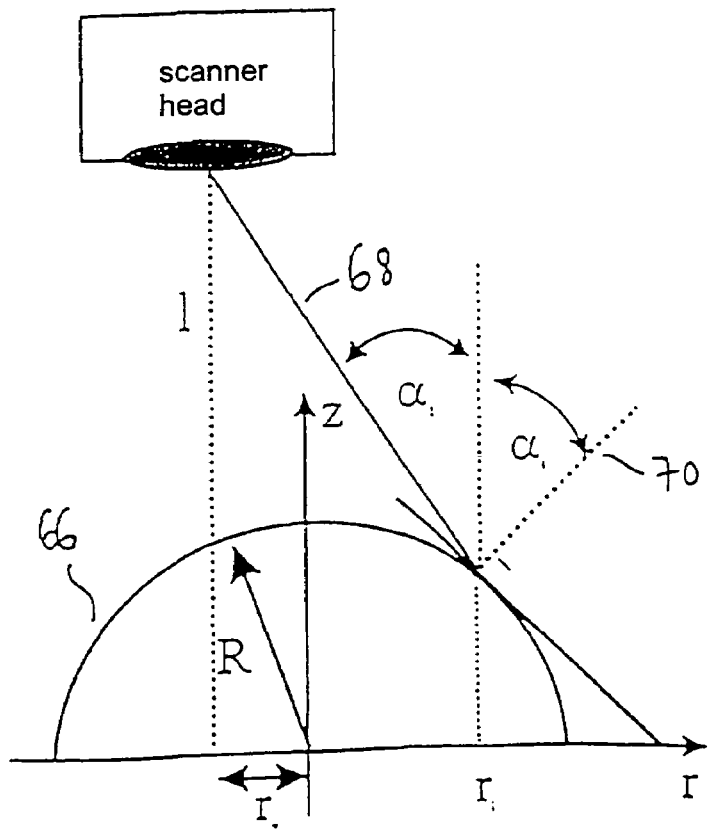
FIG. 11 schematically shows the beam path for non-centred incidence of the laser-beam spot.

In a real system, however, it is rather the situation shown in FIG. 11 which is encountered. The head of the galvanometric scanner 32, represented in FIG. 3, which deflects the laser beam 34 onto the eye 10, is offset relative to the cornea 66, schematically shown here as a semicircle. A laser beam emerging perpendicularly from the scanner head would be incident on the cornea at an offset distance $r_v$ from the z axis. It can furthermore be seen that the angle between the laser beam 68 sent onto the cornea 66 and the normal 70 to the surface is increased from $\alpha_1$ to the angle $\alpha_1+\alpha_2$. This leads to stronger attenuation of the ablation depth on the right-hand side in FIG. 11.

In order to calculate this ablation depth, it is merely necessary to rotate the coordinate system so that the z axis again runs parallel to the laser beam. The formulae indicated above can then once more be applied.

Figure 12:
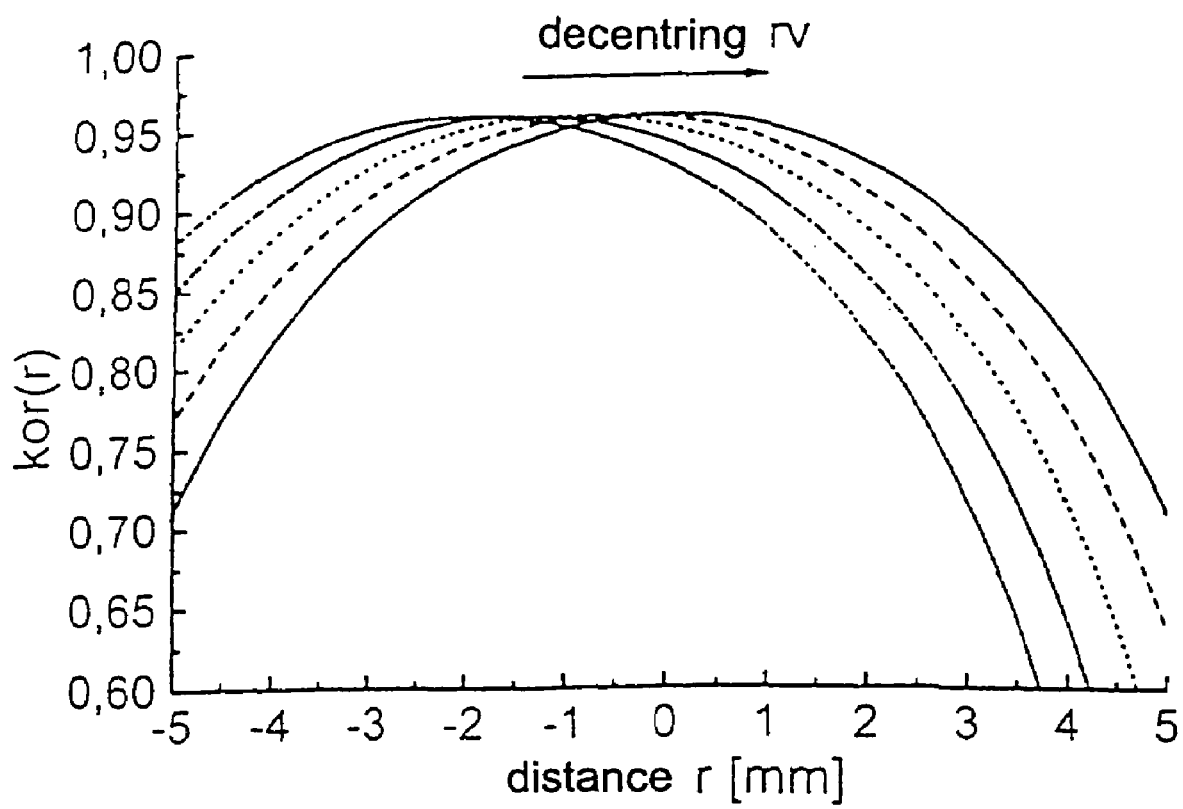
FIG. 12 shows the dependency of the combined correction factor for the ablation depth on the distance r of the incidence point of the laser-beam spot centre on the cornea from the z axis shown in FIG. 11 with a differing degree of the decentring $r_v$ for a radius of curvature R=7.8 mm and a beam energy density F=150 mJ/cm² of the incident laser beam.

The dependency of the correction factor kor(r) on the offset distance $r_v$ is represented by numerical simulation in FIG. 12 for the corneal arrangement shown in FIG. 11. As the offset distance $r_v$ increases, the correction factor kor(r) assumes an increasingly asymmetric shape.

A perfect system therefore takes into account not only the increase in the effective area of the laser-beam spot and the reflection at the corneal surface, but also the effect of the offset. This can be summarised by saying that the effect of the angle between the laser beam and the corneal surface is taken into account.

However, this angle is not always accurately known. The invention can therefore be refined further.

Firstly, the approximation that the cornea is spherical is not generally correct. It is generally aspherical and also often has astigmatism. The cornea therefore has differing radii of curvature at different locations. These radii of curvature can be measured with so-called topography systems. Using this information about the local radius of curvature, on the one hand it is then possible to calculate the angle between the laser beam and the corneal surface, the formula (8) being used. The fraction of the laser-beam energy incident on the corneal surface which is reflected away can thereby be derived from formulae (6) and (7). To calculate the effect of the angle between the laser beam and the corneal surface on the energy density of the laser-beam spot incident on the corneal surface, it is furthermore possible to use formulae (2) and (3), in which case R is then only the local radius of curvature of the cornea.

For further refinement, the fact that the angle between the laser beam and the corneal surface also changes during the ablation should be taken into account. If, for example, a sequence of 50 laser-beam spot pulses were to be necessary according to a previous calculation in order to ablate the cornea according to the ablation profile at a particular location, then it may be that the angle between the laser beam and the corneal surface changes further, after each pulse and therefore each partial ablation, in such a way that a smaller fraction of the laser beam is reflected away, for example, so that only 49 or 48 pulses are needed instead of 50 pulses or, conversely, it may be that the conditions become less favourable during the ablation so that more pulses are needed instead of the 50 pulses originally calculated. Since, according to the formulae indicated above, the extent to which a laser-beam pulse ablates the cornea is known, this effect can already be taken into account a priori in a refined computation. For this calculation, the corneal surface may be simulated on the computer, or the changing local radii of curvature of the cornea may be calculated approximately. The calculation would then be carried out just as in the case discussed in the previous paragraph, with locally differing radii of curvature being incorporated.

As already mentioned above in the description of FIG. 3, the movements of the eye are followed during the ablation. Because of these movements, not only is it naturally necessary to track the ablation profile to be removed, and to control the scanner 32 accordingly, but also the angle between the laser beam and the corneal surface changes during this. This change is preferably also taken into account. The angle with respect to the axis A can be calculated, and the angle between the laser beam and the corneal surface can be derived therefrom.

The present invention has been described with reference to a spot-scanning system, although it can also be employed in full ablation as well as slit-scanning ablation.

Numerically standard approximations may be used for the formulae employed.

The invention claimed is:

1. A method of laser corneal ablation comprising:
   generating a laser-beam profile having one or more elementary laser beams;
   projecting the laser-beam profile onto a cornea and thereby ablating a predetermined ablation profile from the cornea; and
   adjusting the laser-beam profile according to an effect of an angle between the one or more elementary beams of the laser-beam profile and a surface of the cornea on an energy density of the laser-beam profile on the surface of the cornea;
   wherein adjusting the laser-beam profile further comprises increasing a time interval that at least one elementary beam is incident on the corneal surface at an incident point of the corneal surface as a function of the distance of the incident point of the elementary beam center on the cornea from an axis running parallel to the elementary beam direction, which axis meets the corneal surface at a substantially right angle.

2. The method of claim 1 further comprising adjusting the laser-beam profile based on a fraction of the one or more elementary beams incident on the corneal surface that is reflected away.

3. A method of laser corneal ablation comprising:
   generating a laser-beam profile having one or more elementary laser beams;
   projecting the laser-beam profile onto a cornea and thereby ablating a predetermined ablation profile from the cornea;
   adjusting the laser-beam profile according to an effect of an angle between the one or more elementary beams of the laser-beam profile and a surface of the cornea on an energy density of the laser-beam profile on the surface of the cornea; and adjusting the laser-beam profile based on the fact that the energy density F of an emitted elementary beam of radius $r_s$ is reduced to $F/k1(r)$, in the case of a cornea assumed to be substantially hemispherical with radius R, when incident on its curved surface, where $$kl(r) = \frac{A_{eff}(r)}{A_0} = \frac{A_{eff}(r)}{\pi \cdot r_2 2}$$

and $$A_{eff}(r) = \int_{-rs}^{rs}\int \frac{\sqrt{rs^2 - x^2} + r}{\sqrt{rs^2 - x^2} + r} \sqrt{1 + \left(\frac{d}{dx}f(x,y)\right)^2 + \left(\frac{d}{dx}f(x,y)\right)^2}\, dx\, dy$$

with $$z = f(x,y) = f(r) = \sqrt{R^2 - x^2 - y^2} = \sqrt{R^2 - r^2},$$
$$r = (x^2 + y^2)^{1/2},$$

where x, y, z are the coordinates of the incidence point of the elementary beam center in a Cartesian coordinate system in which the origin lies at the sphere centre of the cornea.

4. A method of laser corneal ablation comprising:
generating a laser-beam profile having one or more elementary laser beams;
projecting the laser-beam profile onto a cornea and thereby ablating a predetermined ablation profile from the cornea;
adjusting the laser-beam profile according to an effect of an angle between the one or more elementary beams of the laser-beam profile and a surface of the cornea on an energy density of the laser-beam profile on the surface of the cornea; and
adjusting the laser-beam profile based on a distance r of an incidence point of the center of the one or more elementary beams on the cornea from an axis running parallel to the one or more elementary beam directions which meets the corneal surface at a substantially right angle.

5. A method of laser corneal ablation comprising:
generating a laser-beam profile having one or more elementary laser beams;
projecting the laser-beam profile onto a cornea and thereby ablating a predetermined ablation profile from the cornea; and
adjusting the laser-beam profile according to an effect of an angle between the one or more elementary beams of the laser-beam profile and a surface of the cornea on an energy density of the laser-beam profile on the surface of the cornea;
wherein adjusting the laser-beam profile includes adjusting the ablation depth of the one or more elementary beams based on the determination that the ablation depth due to a particular elementary beam pulse is reduced to $d \cdot kor(r)$ in relation to the ablation depth d in the case of normal incidence of the elementary beam when the elementary beam is incident on the curved surface, where $$kor(r) = \frac{\ln\left(\frac{(1-k2(r)) \cdot F}{k1(r) \cdot F_{th}}\right)}{\ln\left(\frac{F}{F_{th}}\right)}$$

and $F_{th}$ is the energy-density threshold above which ablation takes place.

6. A method of laser corneal ablation comprising:
generating a laser-beam profile having one or more elementary laser beams;
projecting the laser-beam profile onto a cornea and thereby ablating a predetermined ablation profile from the cornea;
adjusting the laser-beam profile according to an effect of an angle between the one or more elementary beams of the laser-beam profile and a surface of the cornea on an energy density of the laser-beam profile on the surface of the cornea; and
adjusting the laser-beam profile based on the fact that in the case of a cornea assumed to be substantially spherical, the unreflected fraction of the energy density $F/k1(r)$ of the one or more elementary beams incident on the curved surface is given as $(1-k2(r)) \cdot F/k1(r)$, where $$k2(r) = \frac{q^2(r) + q^2(r)'}{2},$$

with $$q'(\alpha_1) = \frac{\sqrt{n^2 - \sin^2(\alpha_1)} - \cos(\alpha_1)}{1 - n^2}$$

$$q''(\alpha_1) = \frac{n^2\cos(\alpha_1) - \sqrt{n^2 - \sin^2(\alpha_1)}}{n^2\cos(\alpha_1) + \sqrt{n^2 - \sin^2(\alpha_1)}}$$

where $\pi/2 - \alpha_1$ is the angle between the one or more elementary beams and the corneal surface, where $$\alpha_1(r) = a\tan\left(\frac{r}{\sqrt{R^2 - r^2}}\right) \text{ with } 0 \leq r^2 < R^2.$$

and n is the empirically determined refractive index of the cornea at the wavelength of the one or more elementary beams which are used.

7. A method of laser corneal ablation comprising:
generating a laser-beam profile having one or more elementary laser beams;
projecting the laser-beam profile onto a cornea and thereby ablating a predetermined ablation profile from the cornea;
adjusting the laser-beam profile according to an effect of an angle between the one or more elementary beams of the laser-beam profile and a surface of the cornea on an energy density of the laser-beam profile on the surface of the cornea;
determining the local radius of curvature of the cornea; and
determining the angle between the one or more elementary beams and the surface of the cornea based on the local radius of curvature.

8. A method of laser corneal ablation comprising:
generating a laser-beam profile having one or more elementary laser beams;
projecting the laser-beam profile onto a cornea and thereby ablating a predetermined ablation profile from the cornea; and
adjusting the laser-beam profile according to an effect of an angle between the one or more elementary beams of the laser-beam profile and a surface of the cornea on an energy density of the laser-beam profile on the surface of the cornea;
wherein adjusting the laser-beam profile includes adjusting the laser-beam profile based on the fact that the angle between the elementary beams and the corneal surface changes during the ablation due to the ablation of at least a portion of the corneal surface.

9. A method of laser corneal ablation comprising:
generating a laser-beam profile having one or more elementary laser beams;
projecting the laser-beam profile onto a cornea and thereby ablating a predetermined ablation profile from the cornea;
adjusting the laser-beam profile according to an effect of an angle between the one or more elementary beams of the laser-beam profile and a surface of the cornea on an energy density of the laser-beam profile on the surface of the cornea;
sensing movements of the eye during ablation; and
adjusting the laser-beam profile based on the effect of the eye movements on the energy density of the laser-beam profile on the cornea.

10. A method of laser corneal ablation comprising:
generating a laser-beam profile having one or more elementary laser beams;
projecting the laser-beam profile onto a corneal surface and thereby ablating a predetermined ablation profile from the corneal surface;
adjusting the laser-beam profile according to an effect of an angle between the one or more elementary beams and the corneal surface on the fraction of laser-beam energy incident on the corneal surface which is reflected away;
adjusting the laser-beam profile based on a distance r of an incidence point of the center of the one or more elementary beams on the cornea from an axis running parallel to the one or more elementary beam directions which meets the corneal surface at a substantially right angle.

11. A method of laser corneal ablation comprising:
generating a laser-beam profile having one or more elementary laser beams;
projecting the laser-beam profile onto a corneal surface and thereby ablating a predetermined ablation profile from the corneal surface; and
adjusting the laser-beam profile according to an effect of an angle between the one or more elementary beams and the corneal surface on the fraction of laser-beam energy incident on the corneal surface which is reflected away;
wherein adjusting the laser-beam profile further comprises:
adjusting the laser-beam profile based on the determination that, in the case of a cornea assumed to be substantially hemispherical with radius R, the unreflected fraction of the energy density F of the one or more elementary beams incident on the curved surface is given as $(1-k2(r))\cdot F$, where $$k2(r) = \frac{q_\perp^2(r) + q_\parallel^2(r)}{2},$$

with $$q_\perp(\alpha_1) = \frac{\sqrt{n^2 - \sin^2(\alpha_1)} - \cos(\alpha_1)}{1 - n^2}$$

$$q_\parallel(\alpha_1) = \frac{n^2\cos(\alpha_1) - \sqrt{n^2 - \sin^2(\alpha_1)}}{n^2\cos(\alpha_1) + \sqrt{n^2 - \sin^2(\alpha_1)}}$$

where $\pi/2 - \alpha_1$ is the angle between the one or more elementary beams and the corneal surface, where $$\alpha_1(r) = \operatorname{atan}\left(\frac{r}{\sqrt{R^2 - r^2}}\right) \text{ with } 0 \leq r^2 < R^2.$$

and n is the empirically determined refractive index of the cornea at the wavelength of the one or more elementary beams.

12. A method of laser corneal ablation comprising:
generating a laser-beam profile having one or more elementary laser beams;
projecting the laser-beam profile onto a corneal surface and thereby ablating a predetermined ablation profile from the corneal surface; and
adjusting the laser-beam profile according to an effect of an angle between the one or more elementary beams and the corneal surface on the fraction of laser-beam energy incident on the corneal surface which is reflected away;
wherein adjusting the laser-beam profile includes adjusting the ablation depth of the one or more elementary beams based on the determination that the ablation depth due to a particular elementary beam pulse is reduced to $d \cdot kor(r)$ in relation to the ablation depth d in the case of normal incidence of the elementary beam when the elementary beam is incident on the curved surface, where $$kor(r) = \frac{\ln\left(\frac{(1-k2(r))\cdot F}{k1(r)\cdot F_{th}}\right)}{\ln\left(\frac{F}{F_{th}}\right)}$$

and $F_{th}$ is the energy-density threshold above which ablation takes place.

13. A method of laser corneal ablation comprising:
generating a laser-beam profile having one or more elementary laser beams;
projecting the laser-beam profile onto a corneal surface and thereby ablating a predetermined ablation profile from the corneal surface;
adjusting the laser-beam profile according to an effect of an angle between the one or more elementary beams and the corneal surface on the fraction of laser-beam energy incident on the corneal surface which is reflected away;
determining the local radius of curvature of the cornea; and
determining the angle between the one or more elementary beams and the surface of the cornea based on the local radius of curvature.

14. A method of laser corneal ablation comprising:
generating a laser-beam profile having one or more elementary laser beams;
projecting the laser-beam profile onto a corneal surface and thereby ablating a predetermined ablation profile from the corneal surface; and
adjusting the laser-beam profile according to an effect of an angle between the one or more elementary beams and the corneal surface on the fraction of laser-beam energy incident on the corneal surface which is reflected away;
wherein adjusting the laser-beam profile includes adjusting the laser-beam profile based on the fact that the angle between the elementary beams and the corneal surface changes during the ablation due to the ablation of at least a portion of the corneal surface.

15. A method of laser corneal ablation comprising:
generating a laser-beam profile having one or more elementary laser beams;
projecting the laser-beam profile onto a corneal surface and thereby ablating a predetermined ablation profile from the corneal surface;

adjusting the laser-beam profile according to an effect of an angle between the one or more elementary beams and the corneal surface on the fraction of laser-beam energy incident on the corneal surface which is reflected away;

sensing movements of the eye during ablation; and adjusting the laser-beam profile based on the effect of the eye movements on the energy density of the laser-beam profile on the cornea.

* * * * *

UNITED STATES PATENT AND TRADEMARK OFFICE
CERTIFICATE OF CORRECTION

PATENT NO. : 7,544,194 B2 Page 1 of 1
APPLICATION NO. : 11/109180
DATED : June 9, 2009
INVENTOR(S) : Michael Mrochen et al.

It is certified that error appears in the above-identified patent and that said Letters Patent is hereby corrected as shown below:

Column 18, Line 7, Claim 12, the word "comeal" should be --corneal--

Signed and Sealed this

Twenty-second Day of September, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,544,194 B2 | Page 1 of 1 |
| APPLICATION NO. | : 11/109180 | |
| DATED | : June 9, 2009 | |
| INVENTOR(S) | : Michael Mrochen et al. | |

It is certified that error appears in the above-identified patent and that said Letters Patent is hereby corrected as shown below:

Title Page item 73

Assignee: "Wavelight Technologie AG" should be -- WaveLight Laser Technologie AG --

Signed and Sealed this

Fifteenth Day of February, 2011

David J. Kappos
*Director of the United States Patent and Trademark Office*